United States Patent
Geskin et al.

(10) Patent No.: US 10,473,661 B2
(45) Date of Patent: Nov. 12, 2019

(54) METHOD FOR DIAGNOSIS, PROGNOSIS AND DETERMINATION OF TREATMENT FOR CUTANEOUS T-CELL LYMPHOMA

(71) Applicant: UNIVERSITY OF PITTSBURGH—OF THE COMMONWEALTH SYSTEM OF HIGHER EDUCATION, Pittsburgh, PA (US)

(72) Inventors: Larisa J. Geskin, Riverdale, NY (US); Brittany Lynn O'Neil Dulmage, Pittsburgh, PA (US); Louis D. Falo, Jr., Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 14/819,950

(22) Filed: Aug. 6, 2015

(65) Prior Publication Data
US 2015/0344971 A1  Dec. 3, 2015

Related U.S. Application Data

(63) Continuation of application No. PCT/US2014/015314, filed on Feb. 7, 2014.
(Continued)

(51) Int. Cl.
*G01N 33/574* (2006.01)
*A61K 31/395* (2006.01)
(Continued)

(52) U.S. Cl.
CPC ..... *G01N 33/57426* (2013.01); *A61K 31/192* (2013.01); *A61K 31/395* (2013.01);
(Continued)

(58) Field of Classification Search
None
See application file for complete search history.

(56) References Cited

U.S. PATENT DOCUMENTS

2005/0074761 A1* 4/2005 Bensussan ......... C07K 16/3053
435/6.16
2006/0271309 A1  11/2006 Showe et al.
(Continued)

FOREIGN PATENT DOCUMENTS

EP         1343822 B1   5/2012
WO    WO 2013/071410   5/2013

OTHER PUBLICATIONS

Eppendorf Mastercycler Personal Operating Manual (2004).*
(Continued)

*Primary Examiner* — Craig D Ricci
(74) *Attorney, Agent, or Firm* — Baker Botts L.L.P.

(57) ABSTRACT

The present invention relates to biomarkers associated with CTCL, including TOX, PLS3, KIR3DL2, GATA3 and RUNX3, where increased expression, relative to normal control, of one or more of TOX, PLS3, KIR3DL2, and/or GATA3 is associated with CTCL and decreased expression of RUNX3, relative to normal control, is associated with CTCL. One or more of these biomarkers may be used to diagnose CTCL and/or design and monitor treatment.

8 Claims, 11 Drawing Sheets

| Gene | SS to Norm | MF to Norm | Biological Relevance |
|---|---|---|---|
| T-plastin (PLS3) | 83.00 | 12 | PLS3 is an actin-building protein not normally expressed in T-cells. In lymphocytes, its promoter is demethylated (1). |
| Thymocyte selection-associated high mobility group box protein (TOX) | 21.47 | 1.38 | TOX is a TF highly expressed in the thymus, where T-cells develop. May regulate PLS3 (2). |
| Killer cell immunoglobulin-like receptor 3DL2 (KIR3DL2) | 19.67 | n/a | KIR3DL2 is important to the immune response in T-cells (3). |
| Integrin β1 (ITGB1) | 16.67 | 3.19 | ITGB1 plays a role in cellular shape, motility, and the cell cycle. In SS, it may increase skin homing (4). |
| Programmed Cell Death 6 (PDCD6) | 13 | 0.16 | PDCD6 product participates in T cell receptor-programmed cell death (5). |

Related U.S. Application Data

(60) Provisional application No. 61/762,167, filed on Feb. 7, 2013.

(51) Int. Cl.

| | | |
|---|---|---|
| *A61K 31/192* | (2006.01) | |
| *A61K 31/519* | (2006.01) | |
| *A61N 5/10* | (2006.01) | |
| *A61N 5/06* | (2006.01) | |
| *C12Q 1/6886* | (2018.01) | |
| *C12N 15/113* | (2010.01) | |

(52) U.S. Cl.
CPC ............ *A61K 31/519* (2013.01); *A61N 5/062* (2013.01); *A61N 5/10* (2013.01); *C12Q 1/6886* (2013.01); *G01N 33/57407* (2013.01); *A61N 2005/0661* (2013.01); *C12N 15/113* (2013.01); *C12N 2310/14* (2013.01); *C12Q 2600/106* (2013.01); *C12Q 2600/158* (2013.01)

(56) References Cited

U.S. PATENT DOCUMENTS

| | | |
|---|---|---|
| 2008/0274468 A1 | 11/2008 | Bensussan et al. |
| 2010/0035971 A1 | 2/2010 | Ranki et al. |
| 2012/0064081 A1 | 3/2012 | Anfossi et al. |
| 2012/0288499 A1 | 11/2012 | Bensussan et al. |

OTHER PUBLICATIONS

Chuang et al (Oncogene 29:2605-2615, 2010).*
Kari et al (J Exp Med 197:1477-1488, 2003).*
World Health Organization (available online at http://www.who.int/suggestions/faq/en/, accessed May 26, 2017.*
The Lancet (vol. 373(9666):781, 2009).*
Maisel (Psychology Today, available online at https://www.psychologytoday.com/blog/rethinking-psychology/201111/what-do-we-mean-normal, dated Nov. 15, 2011).*
Dulmage et al (Oncotarget, Advance Publications, pp. 1-10, 2015).*
Booken et al., "Sezary syndrome is a unique cutaneous T-cell lymphoma as identified by an expanded gene signature including diagnostic marker molecules CDO1 and DNM3," Leukemia 22:393-399 (2008).
Dulmage and Geskin, "Lessons learned from gene expression profiling of cutaneous T-cell lymphoma," Br. J. Dermatol. 169:1188-1197 (2013).
Dulmage, "Three components of the TOX-RUNX3 pathway are differentially expressed in cutaneous T cell lymphoma," In: 2013 Scientific Meeting of Medical Fellows, HHMI, May 2013, See p. 24, left column.
International Search Report and Written Opinion dated May 1, 2014 in International Application No. PCT/US2014/015314.
Kari et al., "Classification and prediction of survival in patients with the Leukemic phase of cutaneous T cell lymphoma," The Journal of Experimental Medicine, vol. 197, No. 11, pp. 1477-1488 (Jun. 2, 2003).
Kim et al., "Long-term Outcome of 525 Patients with Mycosis Fungoides and Sezary Syndrome," Arch. Dermatol. 139(7):857-866 (2003).
Lessin et al., "Topical Chemotherapy in Cutaneous T-cell Lymphoma," JAMA Dermatol. 149(1):25-32 (2013).
Nebozhyn et al., "Quatitative PCR on 5 genes reliably identifies CTCL patients with 5% to 99% circulating tumor cells with 90% accuracy," Blood 107(8):3189-3196 (2006).
van Doom et al., "Aberrant Expression of the Tyrosine Kinase Receptor EphA4 and the Transcription Factor Twist in Sezary Syndrome Identified by Gene Expression Analysis," Cancer Res 64:5578-5586 (2004).
Weberschock et al., "Interventions for mycosis fungoides (Review)," Cochrane Database Syst. Rev. Issue 9, Art No. CD008946 (2012).
Zhang et al., "Molecular Markers of Early-Stage Mycosis Fungoides," J Invest Dermatol 132:1698-1706 (2012).

* cited by examiner

FIGURE 1

| Gene | SS to Norm | MF to Norm | Biological Relevance |
|---|---|---|---|
| T-plastin (PLS3) | 83.00 | 12 | PLS3 is an actin-building protein not normally expressed in T-cells. In lymphocytes, its promoter is demethylated (1). |
| Thymocyte selection-associated high mobility group box protein (TOX) | 21.47 | 1.38 | TOX is a TF highly expressed in the thymus, where T-cells develop. May regulate PLS3 (2). |
| Killer cell immunoglobulin-like receptor 3DL2 (KIR3DL2) | 19.67 | n/a | KIR3DL2 is important to the immune response in T-cells (3). |
| Integrin β1 (ITGB1) | 16.67 | 3.19 | ITGB1 plays a role in cellular shape, motility, and the cell cycle. In SS, it may increase skin homing (4). |
| Programmed Cell Death 6 (PDCD6) | 13 | 0.16 | PDCD6 product participates in T cell receptor-programmed cell death (5). |

FIGURE 2B-D
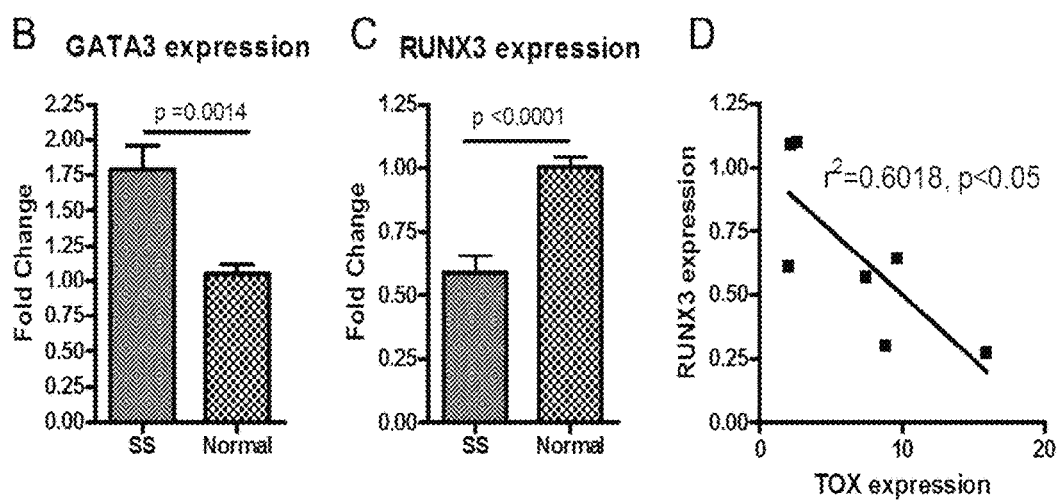

FIGURE 5A-B
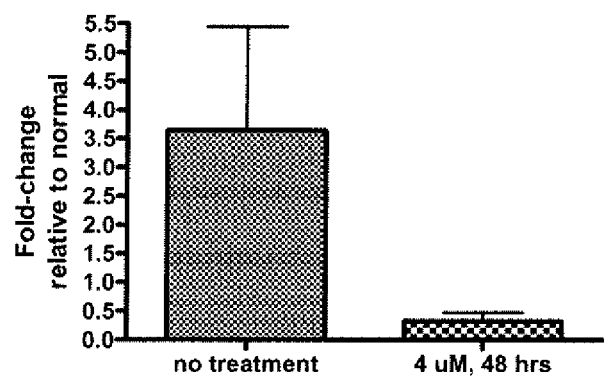
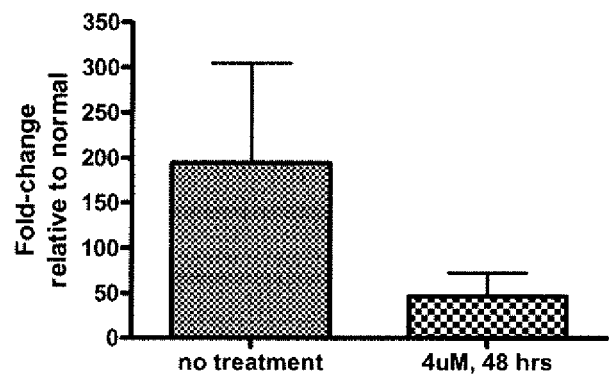

METHOD FOR DIAGNOSIS, PROGNOSIS AND DETERMINATION OF TREATMENT FOR CUTANEOUS T-CELL LYMPHOMA

PRIORITY CLAIM

This Application is a continuation of International Patent Application No. PCT/US2014/015314, filed Feb. 7, 2014 and claims priority to U.S. Provisional Application No. 61/762,167, filed Feb. 7, 2013, to both of which priority is claimed and the contents of both of which are incorporated herein in their entireties.

GRANT INFORMATION

This invention was made with government support under Grants Nos. CA 121973, UL1TR000005 and RR024153 awarded by the National Institutes of Health. The government has certain rights in the invention.

INTRODUCTION

The present invention relates to biomarkers of cutaneous T-cell lymphoma and Sézary Syndrome which may be used to diagnose these conditions and guide therapeutic regimens.

BACKGROUND OF THE INVENTION

T-cell lymphoma that involves the skin is generally known as cutaneous t-cell lymphoma (CTCL). The term CTCL encompasses a number of disorders, including mycosis fungoides (MF), which is the most common form of CTCL. Sézary syndrome (SS) is an advanced, variant form of mycosis fungoides, characterized by the presence of malignant lymphocytes in the blood. See "Getting the Facts" monograph for "Cutaneous T Cell Lymphoma" published by the Lymphoma Research Foundation, 115 Broadway Suite 1301, New York N.Y. 10006 (last update January 2013). No specific diagnostic or prognostic markers exist to enable early diagnosis of MF, SS and CTCL. The pathogenesis of CTCL is unknown and there are no therapeutic targets available for disease-specific therapies. Because no specific diagnosis is possible, CTCL is often confused with other inflammatory dermatoses, such as psoriasis or eczema, and patients often live with the disease for years before a correct diagnosis is established. If diagnosed early, CTCL patients have a longer lifespan, but the survival rate goes down as CTCL reaches advanced stages. Thus, a diagnostic test that could easily confirm the presence of CTCL early in disease course is needed.

SUMMARY OF THE INVENTION

The present invention relates to biomarkers associated with CTCL and/or MF or SS in particular, including TOX, PLS3, KIR3DL2, GATA3 and RUNX3, where increased expression, relative to normal control, of one or more of TOX, PLS3, KIR3DL2, and/or GATA3 is associated with CTCL and decreased expression of RUNX3, relative to normal control, is associated with CTCL. Detection of these and/or a subset of these biomarkers may be used to diagnose CTCL and/or design and monitor treatment.

BRIEF DESCRIPTION OF THE FIGURES

FIG. 1. Genes selected for further study, showing expression, relative to norm, in Sézary syndrome (SS) and mycosis fungoides (MF).

FIGS. 2A-G. Relative expression of (A) PLS3, KIR3DL2 and TOX, (B) GATA3 and (C) RUNX3 in SS versus normal CD4+ cells. (D) Expression levels of RUNX3 and TOX were inversely related. (E) Results of qRT-PCT (dark bars) versus sequence-based transcriptome analysis (light bars) for TOX, KIR3DL2 and PLS3. (F) TOX expression in individual subjects. (G) PLS3 expression in individual subjects.

FIGS. 5A-C. Following romidepsin treatment, expression of (A) TOX; (B) PLS3 and (C) RUNX3 genes were measured.

DETAILED DESCRIPTION OF THE INVENTION

Figure 2A:
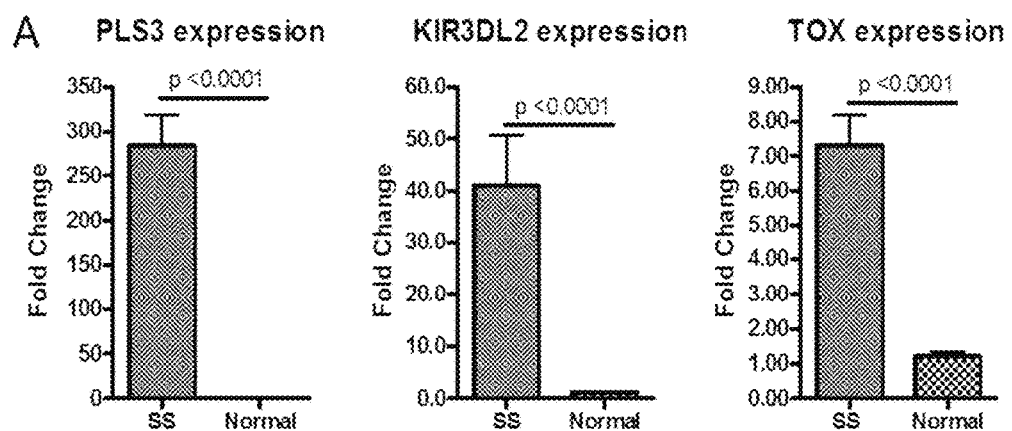

The present invention relates to biomarkers for CTCL and associated disorders (for example SS and/or MF) which may also serve as therapeutic targets. In certain non-limiting embodiments, the present invention provides for a method of diagnosing CTCL or an associated disorder in a subject comprising determining the level of expression of one or more (or two or more or three or more or four or more or five or more or six or more or seven) of TOX, PLS3, KIR3DL2, GATA3, ITGB1, PDCD6 and/or RUNX3 in a sample of cells of a subject, relative to gene expression in a normal healthy subject, where increased expression in one or more of TOX, PLS3, KIR3DL2 and/or GATA3 indicates a diagnosis of CTCL and/or decreased expression of RUNX3 indicates a diagnosis of CTCL. In certain non-limiting embodiments, the biomarkers tested include at least RUNX3. In certain non-limiting embodiments, the biomarkers tested include at least TOX. In certain non-limiting embodiments, the biomarkers tested include at least KIR3DL2. Where the marker is TOX or ITGB1, an increased level which is increased less than five-fold relative to normal indicates a diagnosis of the CTCL, MF. Where the marker is TOX, KIR3DL2, ITGB1 or PDCD6, an increased level which is increased more than five-fold or more than 10-fold relative to normal indicates a diagnosis of the CTCL, SS.

In certain non-limiting embodiments, the present invention provides for a method of diagnosing CTCL or an associated disorder in a subject comprising determining the level of expression of RUNX3 in a sample of cells of a subject, relative to gene expression in a normal healthy subject, where decreased expression of RUNX3 indicates a diagnosis of CTCL. Related embodiments, in addition to determining expression of RUNX3, further comprise determining the level of expression of one or more (or two or more or three or more or four or more or five or more or six) of TOX, PLS3, KIR3DL2, ITGB1, PDCD6 and/or GATA3 in a sample of cells of a subject, relative to gene expression in a normal healthy subject, where increased expression in one or more of TOX, PLS3, KIR3DL2, ITGB1, PDCD6 and/or GATA3 indicates a diagnosis of CTCL. In certain non-limiting embodiments, the biomarkers tested include, in addition to RUNX3, at least TOX. In certain non-limiting embodiments, the biomarkers tested include, in addition to RUNX3, at least KIR3DL2. In certain non-limiting embodiments, the biomarkers tested include, in addition to RUNX3, at least PLS3. Where the marker is TOX or ITGB1, an increased level which is increased less than five-fold relative to normal indicates a diagnosis of the CTCL, MF. Where the marker is TOX, KIR3DL2, ITGB1 or PDCD6, an increased level which is increased more than five-fold or more than 10-fold relative to normal indicates a diagnosis of the CTCL, SS. Where the marker is PLS3, an increased level which is increased more than ten-fold relative to normal indicates a diagnosis of CTCL and an increased level which is increased more than 50 fold indicates SS. The subject is a human subject. In non-limiting embodiments, the subject has a skin lesion. In non-limiting embodiments, the subject has leukemic cells, for example but not limited to in a peripheral blood sample. In non-limiting embodiments, the subject has a skin lesion and leukemic cells.

Expression levels may be determined, for example, by determining, in a sample of cells from a subject (e.g. a human subject), levels of RNA (for example, using PCR analysis (or other method which includes amplification of RNA in the sample), array analysis, Northern blot analysis, or any method known in the art) or by determining levels of protein expression (for example using antibodies or related molecules (e.g. single chain antibodies, antibody fragments, etc) or any method known in the art). Non-limiting specific examples of methods of measurement may comprise antibody-binding, sequencing, probe hybridization, real-time quantitative reverse transcription polymerase chain reaction ("RT-q PCR"), real time PCR, Northern blot, immunohistochemistry, and/or Western blot.

In one specific non-limiting embodiment, TOX may have NCBI Reference Sequence NP_055544.1, Accession No. NP_055544 XP_376776.

In one specific non-limiting embodiment, PLS3 may have NCBI Reference Sequence NP_001129497.1, Accession No. NP_001129497 and/or see Lin et al., 1999, DNA Cell Biol. 18:27-37.

In one specific non-limiting embodiment, for KIR3DL2, see NCBI Gene ID No. 3812.

In one specific non-limiting embodiment, GATA3 may have NCBI Reference Sequence NP_001002295.1, Accession No. NP_001002295.

In one specific non-limiting embodiment, RUNX3 may have GeneBank No. AAH13362.1, Accession No. AAH13362.

In one specific non-limiting embodiment, ITGB1 may have GenBank No. AAI13902, Accession No. AAI13902.

In one specific non-limiting embodiment, PDCD6 may have GenBank No. AAH50597.1, Accession No. AAH50597.

In certain non-limiting embodiments the sample of cells is obtained from a region of diseased tissue in the subject or may be obtained from a blood sample. For example, but not by way of limitation, the sample may be peripheral blood mononuclear cells, or CD4+ T cells, or cells from tissue affected by the disease such as cells from a skin lesion.

In related embodiments, the invention provides for kits comprising a means of determining expression levels of one or more (or two or more or three or more or four or more or five or more or six or more or seven) of TOX, PLS3, KIR3DL2, GATA3, ITGB1, PDCD6 and/or RUNX3, optionally together with a positive and/or negative control. Such means may comprise, for example but not by way of limitation, an antibody or fragment thereof or single chain antibody specific for the biomarker or biomarkers to be detected, and/or a nucleic acid probe or primer specific for the biomarker or biomarkers tested; these may be directly detectable themselves or indirectly detectable, for example using a labeled secondary antibody or probe or a substrate.

An indication of a diagnosis of a CTCL would be desirably considered in conjunction with clinical features of a subject's presentation to confirm a diagnosis, for example the appearance, symptomatology and histopathology of skin lesions or the presence of atypical lymphocytes in the blood. A positive result showing increased expression of one or more of these genes may be followed by one or more further diagnostic measure, for example, tissue histopathologic analysis, evaluation of PBMC to look for leukemic cells, and/or one or more therapeutic measure to treat CTCL.

The present invention is further based, at least in part, on the discovery that the expression levels of these genes can change in response to various treatments. Accordingly, the present invention provides a method for determining an effective treatment regimen for a subject suffering from CTCL comprising obtaining a cell sample from the subject, determining the expression level of one or more (or two or more or three or more or four or more or five) of TOX, PLS3, KIR3DL2, GATA3, and/or RUNX3 in the cells, exposing cells in the sample to a candidate CTCL therapeutic agent, and determining the expression level of the gene(s) in treated cells, where a decrease in the expression of one or more of TOX, PLS3, KIR3DL2 and/or GATA3 in response to treatment and/or an increase in expression of RUNX3, resulting from treatment, indicates that the agent would be a beneficial therapy for the subject; such method may be followed by treating the subject with the agent. Similarly, the expression level of one or more of TOX, PLS3, KIR3DL2, GATA3 and/or RUNX3 may be monitored in cells of a subject during the course of CTCL therapy, where a decrease in TOX, PLS3, KIR3DL2 and/or GATA3 and/or an increase in RUNX3 following treatment would be indicative of therapeutic benefit. In a certain non-limiting embodiment, the invention provides for a method for determining an effective treatment regimen for a subject suffering from cutaneous T-cell lymphoma, comprising determining the expression level of one or more of TOX, PLS3, KIR3DL2, GATA3, and/or RUNX3 in a sample of cells from the subject prior to treatment with a therapeutic agent, administering the therapeutic agent to the subject, and then determining the expression level of one or more of TOX, PLS3, KIR3DL2, GATA3, and/or RUNX3 in a sample of cells from the subject during or following treatment with the therapeutic agent, where a decrease in the expression of one or more of TOX, PLS3, KIR3DL2 and/or GATA3 in response to treatment and/or an increase in expression of RUNX3, resulting from treatment, indicates that the agent has therapeutic benefit. It may be desirable to attempt to treat a subject with a less-agressive form of therapy, where biomarkers indicate a therapeutic benefit. Further, an increase in one or more of TOX, PLS3, KIR3DL2 and/or GATA3 expression and/or a decrease in RUNX3 could indicate a need for more aggressive therapy. For example but not by way of limitation a decrease of TOX, PLS3, KIR3DL2 and/or GATA3 associated with therapeutic benefit may be a decrease of at least about 30 percent or at least about 50 percent relative to pre-treatment levels. For example but not by way of limitation an increase in RUNX3 indicative of therapeutic benefit may be an increase of at least about 30 percent or at least about 50 percent relative to pre-treatment level. In certain non-limiting embodiments, the biomarkers tested include at least RUNX3. In certain non-limiting embodiments, the biomarkers tested include at least TOX. In certain non-limiting embodiments, the biomarkers tested include at least PLS3. In certain non-limiting embodiments, the biomarkers tested include at least KIR3DL2. In certain non-limiting embodiments, the biomarkers tested include at least TOX and RUNX3. In certain non-limiting embodiments, the biomarkers tested include at least PLS3 and RUNX3.

In particular non-limiting embodiments, the therapeutic agent may be corticosteroid, retinoid, imiquimod, radiation, methotrexate, UV light, romidepsin (e.g., Istodax®), photophoresis, noscapine (e.g., Targetin) or a noscapine analog, pralatrexate (e.g., Folotyn®), bortezomib (e.g., Velcade®), denileukin diftitox (e.g., Ontak®), vorinostat (e.g., Zolinza®), mechlorethamine gel (e.g., Valchlor™), alemtuzumab (e.g., Campath®), liposomal doxorubicin, gemcitabine (e.g., Gemzar®), everolimus (e.g., Afinitor®), lenalidomide (e.g., Revlimid®), brentuximab vedotin (Adcetris®), panobinostat, forodesine, AP0866 (a.k.a. Daporinad), mogamulizumab (KWO761), or a combination thereof. In particular non-limiting embodiments, the therapeutic agent is a histone deacetylase inhibitor. Non-limiting examples of "less-aggressive" therapeutic agents include corticosteroid, retinoid, imiquimod, radiation, methotrexate, and UV light phototherapy and photophoresis; non-limiting examples of more aggressive therapeutic agents include noscapine (e.g., Targetin) or a noscapine analog, pralatrexate (e.g., Folotyn®), bortezomib (e.g., Velcade®), denileukin diftitox (e.g., Ontak®), vorinostat (e.g., Zolinza®), and mechlorethamine gel (e.g., Valchlor); and non-limiting examples of even more aggressive agents include alemtuzumab (e.g., Campath®), liposomal doxorubicin, and gemcitabine (e.g., Gemzar®).

See also Lessin et al., 2013, JAMA Dermatol. 149(1):25-32; Weberschock et al., 2012, Cochrane Database Syst. Rev. September 12; 9:CD008946; and Kim et al., 2003, Arch. Dermatol. 139(7):857-866.

In still further embodiments, the present invention provides a method of treating CTCL comprising administering, to a subject in need of such treatment, an agent that reduces expression of TOX, where such agent is siRNA, antisense RNA, or a catalytic DNA or RNA which degrades TOX mRNA.

EXAMPLE 1

Components of the TOX-RUNX3 Pathway are Differentially Expressed in Cutaneous T-Cell Lymphoma A sequence-based transcriptome approach that focuses on malignant cells in Sézary Syndrome (SS) and mycosis fungoides (MF) was used to identify genes that are dysregulated in CTCL and which may serve as biomarkers or targets for treatment. Five genes were selected for further study, namely T-plastin (PLS3), Thymocyte selection-associated high mobility group box protein (TOX), Killer cell immunoglobulin-like receptor 3DL2 (KIR3DL2), Integrin β1 (ITGB1) and Programmed cell death 6 (PDCD6) (FIG. 1).

Quantitative real-time polymerase chain reaction (qRT-PCR) was used to measure expression of genes in CD4+ T cells from SS patients versus normal controls. Table 1 shows the profiles of the SS patients studied.

TABLE 1

| Patient | Age/Sex/Race | Diagnosis, Stage | Current Tx |
| --- | --- | --- | --- |
| 1 | 58 WM | T3N1M0B2/Stage IVA1, SS | Romidepsin |
| 2 | 80 WF | T3N0M0B2/Stage IVA1, SS | Photophoresis, Targetin |
| 3 | 42 AAF | T3N1M0B2/Stage IVA1, SS | Romidepsin |

TABLE 1-continued

| Patient | Age/Sex/Race | Diagnosis, Stage | Current Tx |
| --- | --- | --- | --- |
| 4 | 67 WF | T3N0M0B2/Stage IVA1, SS | Photophoresis |
| 5 | 67 WM | T3N0M0B2/Stage IVA1, SS | Romidepsin |
| 6 | 86 WF | T3N0M0B2/Stage IIB, MF | Pralatrexate, Targtrin |

Figure 2E:
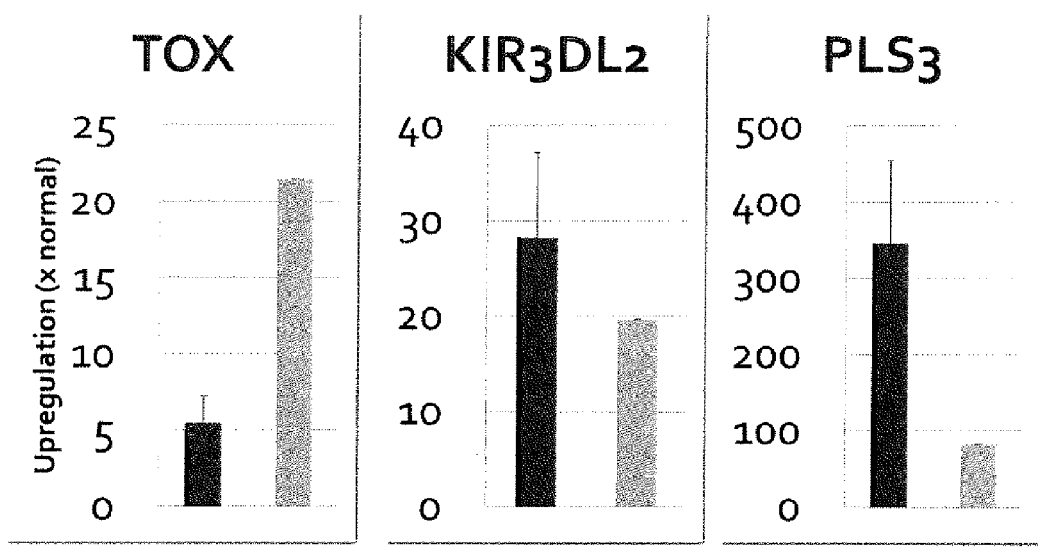
Figure 2F:
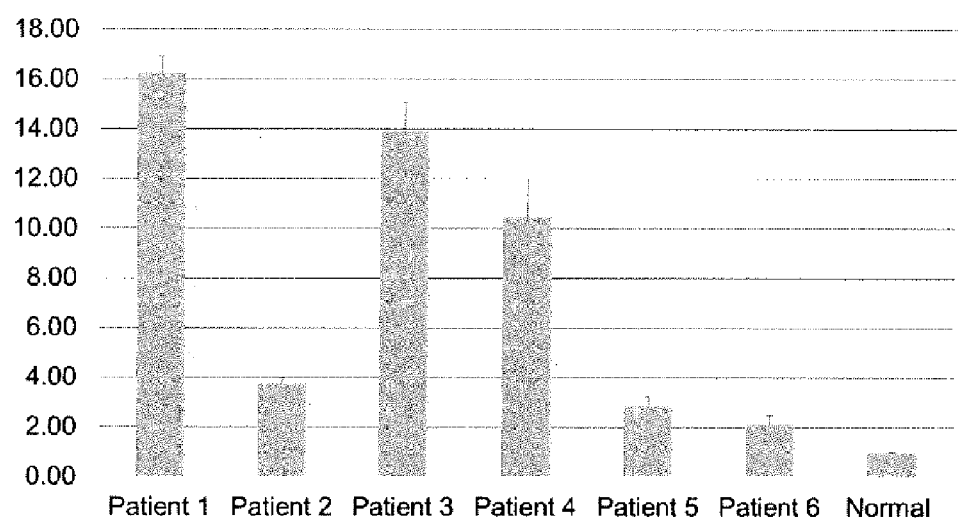
Figure 2G:
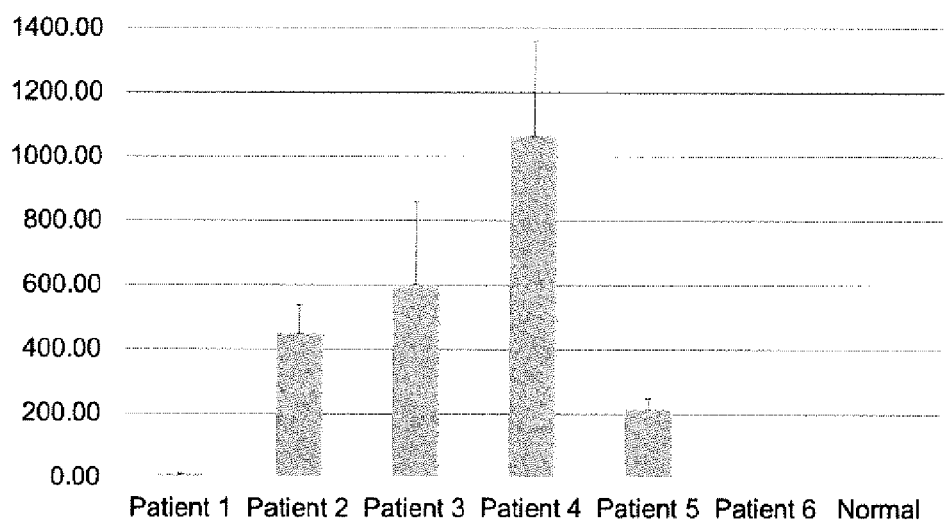

As shown in FIGS. 2A-B, expression of PLS3, KIR3DL2, TOX and GATA3 were all relatively increased in the CD4+ cells of SS patients, whereas expression of RUNX3 was relatively decreased (FIG. 2C). Expression levels of RUNX3 and TOX were inversely related (FIG. 2D). Results of qRT-PCT versus sequence-based transcriptome analysis for TOX, KIR3DL2 and PLS3 are shown in FIG. 2E. TOX expression in individual subjects is shown in FIG. 2F and PLS3 expression in individual subjects is shown in FIG. 2G.

Figure 3:
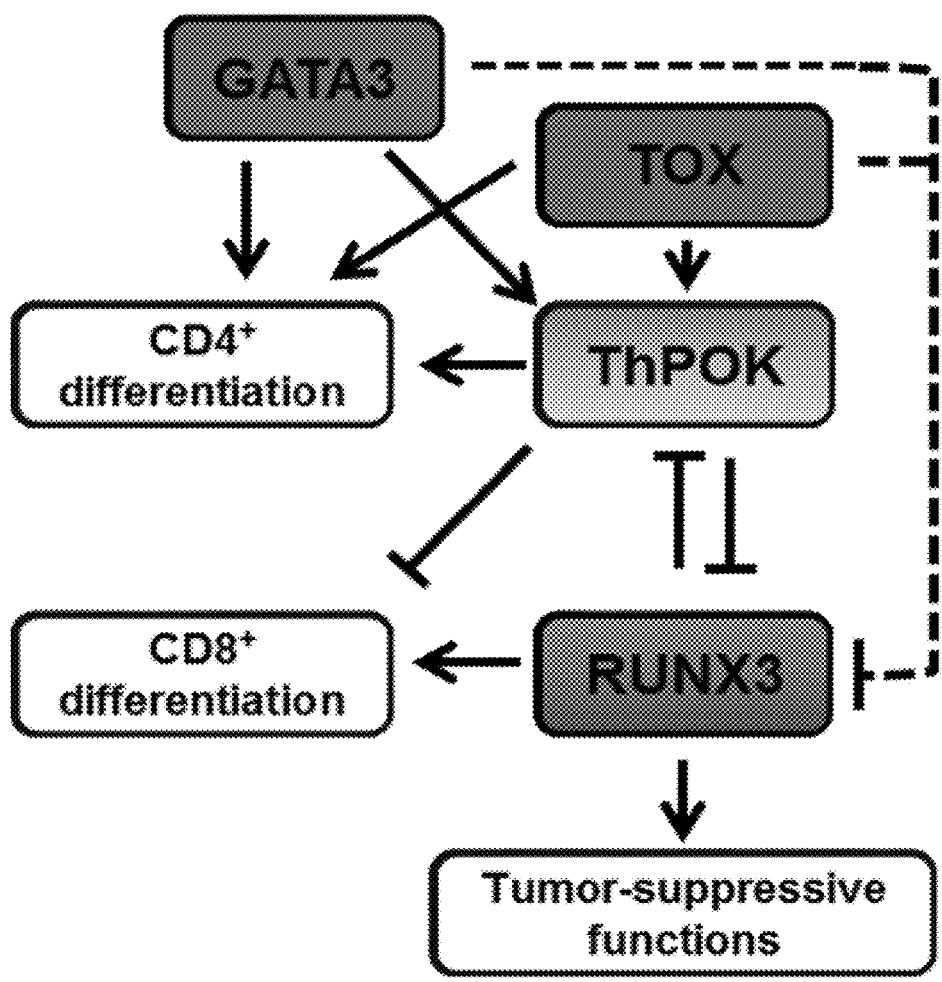
FIG. 3. Three components of the TOX-RUNX3 pathway are dysregulated.

TOX is a transcription factor with known downstream effects (Collins A et al. Nat Rev Imm. 9: 106-115. 2009) and RUNX3 is a tumor suppressor (Chuang L S H et al. Oncogene. 29: 2605-2615. 2010). The data shown in FIGS. 2A-C indicate that in CD4+ cells of SS patients, three components of the TOX-RUNX3 pathway are dysregulated (FIG. 3).

Figure 4:
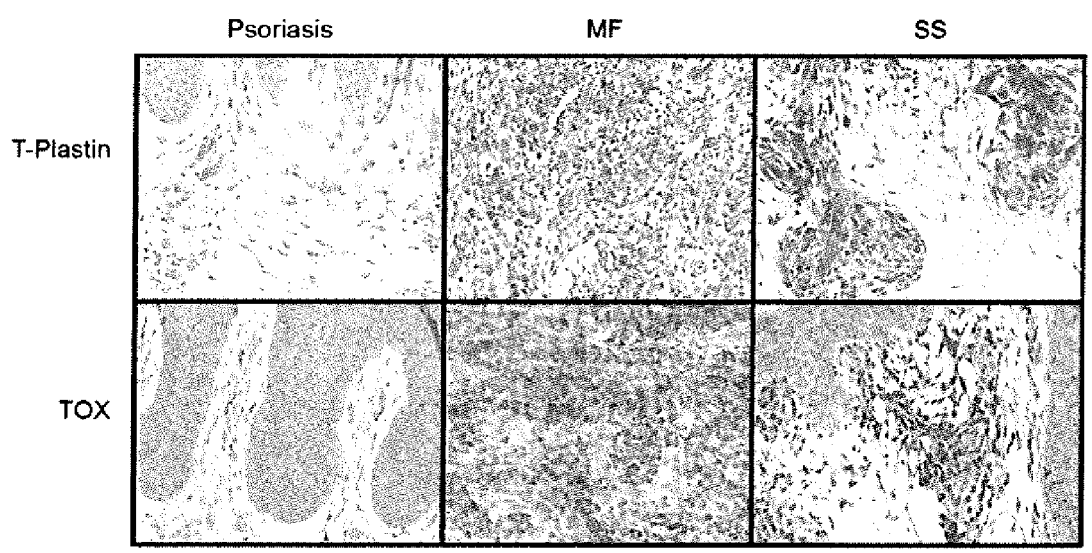
FIG. 4. Expression of TOX and PLS3 (T-Plastin) in psoriasis, MF and SS.

TOX and PLS3 may be used as diagnostic markers to distinguish psoriasis, SS and MF where expression is substantially elevated in SS and MF relative to expression in psoriasis (FIG. 4); TOX and PLS3 may also be used as markers in diagnosis of CTCL.

EXAMPLE 2

Isolated PBMCs were cultured overnight and the next day divided into two treatment groups: 4 μM romidepsin and 20 uM pralatrexate. Each treatment was added 24 hours following culture initiation and was replaced along with fresh media 24 hours after initial treatment. After 48 hours of incubation with treatment, RNA was isolated from treated cells using RNAprotect and RNeasy (Qiagen, Valencia, Calif.) per manufacturer's instructions. For cDNA synthesis, total RNA (100 ng) was used for Reverse Transcription (RT) with Superscript II reverse transcriptase (Life Technologies, Gaithersburg, Md.) using oligo dT primers according to the recommendations of the manufacturer. 2 ul of the resulting cDNA was used for each PCR reaction. Quantitative reverse transcription PCR was performed using TaqMan PCR master mix (Applied Biosystems, Foster City, Calif.) together with TaqMan probes and primers (Applied Biosystems) using standard conditions. Expression of TOX, PLS3 and RNX3 genes were measured in this way.

Figure 5C:
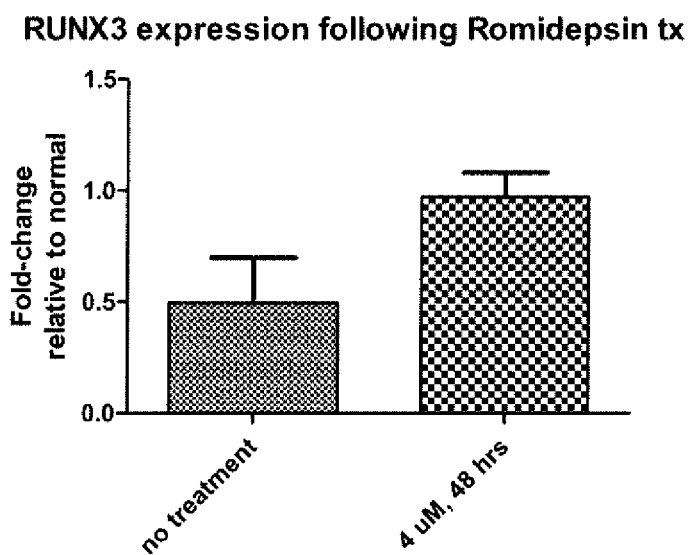

Treatment with romidepsin decreased gene expression of both TOX and PLS3 ($p<0.05$) (FIGS. 5A-B), and increased expression of RUNX3 ($p<0.05$) (FIG. 5C) resulting in normalization of gene expression. Treatment with pralatrexate did not result in altered gene expression of any gene tested.

EXAMPLE 3

5 ng of TOX Silencer Select Validated siRNA (Ambion, Carlsbad, Calif.) was added along with 1.5 μL of TransIT-siQUEST Transfection Reagent (Mirus, Madison, Wis.) per manufacturer's instruction to cultured PBMCs from patients 24 hours after culture was initiated. 72 hours later, RNA was isolated from treated cells using RNAprotect and RNeasy (Qiagen, Valencia, Calif.) per manufacturer's instructions.

For cDNA synthesis, total RNA (100 ng) was used for Reverse Transcription (RT) with Superscript II reverse transcriptase (Life Technologies, Gaithersburg, Md.) using oligo dT primers according to the recommendations of the manufacturer. 2 µl of the resulting cDNA was used for each PCR reaction. Quantitative reverse transcription PCR was performed using TaqMan PCR master mix (Applied Biosystems, Foster City, Calif.) together with TaqMan probes and primers (Applied Biosystems) using standard conditions.

Figure 6:
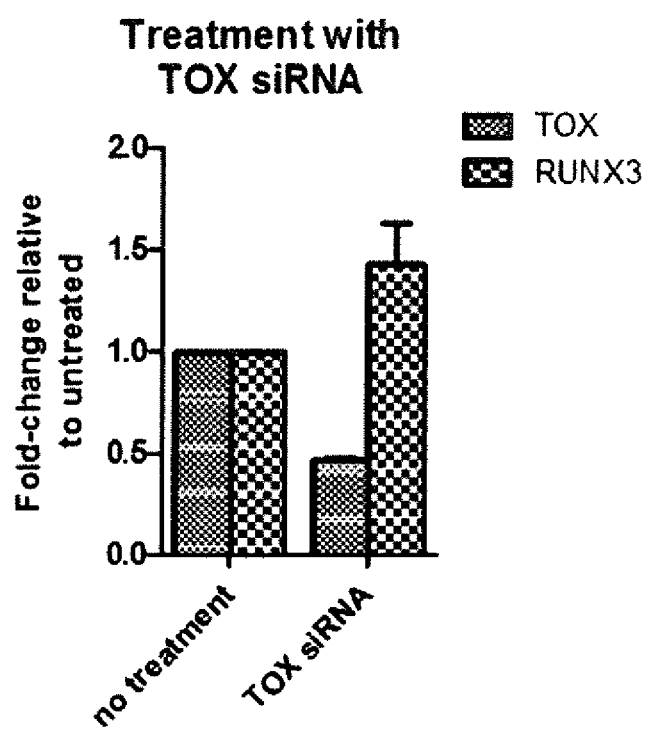
FIG. 6. Fold-change relative to untreated of TOX and RUNX3 gene expression after treatment with TOX siRNA.

As shown in FIG. 6, siRNA knockdown of TOX resulted in decreased TOX expression and increased RUNX3 expression. siRNA knockdown of PLS3 also was found to decrease PLS3 expression.

REFERENCES

1. Booken, N., A. Gratchev, et al. (2008). "Sezary syndrome is a unique cutaneous T-cell lymphoma as identified by an expanded gene signature including diagnostic marker molecules CDO1 and DNM3." Leukemia 22: 393-399.
2. van Doom, R., R. Dijkman, et al. (2004). "Aberrant Expression of the Tyrosine Kinase Receptor EphA4 and the Transcription Factor Twist in Sezary Syndrome Identified by Gene Expression Analysis" Cancer Res 64: 5578-5586.
3. Nebozhyn, M., A. Loboda, et al. (2006). "Quatitative PCR on 5 genes reliably identifies CTCL patients with 5% to 99% circulating tumor cells with 90% accuracy." Blood 107: 3189-3196.
4. Zhang, Y., Y. Wang, et al. (2012). "Molecular Markers of Early-Stage Mycosis Fungoides." J Invest Dermatol 132: 1698-1706.
5. US 20060271309 A1, Method of Diagnosis of Cancer Based on Gene Expression Profiles in Cells, Showe et al.
6. US 20120288499 A1, Methods for diagnosis and treatment of Cutaneous T cell lymphomas, Bensussan et al.
7. US 20080274468 A1, Novel means for diagnosis and therapy of CTCL, Bensussan et al.
8. US 20100035971 A1, Methods and means related to diseases, Ranki et al.
9. Dulmage and Geskin (2013) "Lessons learned from gene expression profiling of cutaneous T-cell lymphoma." Br. J. Dermatol. 169:1188-1197.
10. Lessin et al., 2013, JAMA Dermatol. 149(1):25-32.
11. Weberschock et al., 2012, Cochrane Database Syst. Rev. September 12; 9:CD008946.
12. Kim et al., 2003, Arch. Dermatol. 139(7):857-866.

Various publications are cited herein, the contents of which are hereby incorporated by reference in their entireties.

What is claimed is:

1. A kit for diagnosing cutaneous T-cell lymphoma in a human subject, comprising:
    (i) a positive control sample, wherein the positive control sample has increased expression levels of TOX, PLS3, KIR3DL2, and GATA3, and decreased expression level of RUNX3, relative to the expression levels of TOX, PLS3, KIR3DL2, GATA3 and RUNX3 in a subject who does not suffer from cutaneous T-cell lymphoma; and
    (ii) nucleic acid primers for determining expression levels of TOX, PLS3, KIR3DL2, GATA3, and RUNX3 in a sample obtained from a human subject and in the positive control sample,
    wherein a diagnosis of cutaneous T-cell lymphoma is obtained when, in the sample obtained from the human subject and in the positive control, the determined expression level of TOX is more than 5 fold, the determined expression level of PLS3 is more than 10 fold, the determined expression level of KIR3DL2 is more than 5 fold, the determined expression level of GATA3 is more than about 1.75 fold, and the determined expression level of RUNX3 is less than about 60%, relative to the expression levels of a subject who does not suffer from cutaneous T-cell lymphoma.

2. The kit of claim 1, wherein the expression levels of TOX, PLS3, KIR3DL2, GATA3, and RUNX3 are determined by a polymerase chain reaction (PCR) and/or a real-time PCR.

3. The kit of claim 1, wherein the expression levels of TOX, PLS3, KIR3DL2, GATA3, and RUNX3 are determined by a quantitative real-time PCR and/or a quantitative reverse transcription PCR.

4. The kit of claim 1, wherein the sample obtained from the human subject is a blood sample.

5. The kit of claim 1, wherein the sample obtained from the human subject comprises peripheral blood mononuclear cells obtained from the human subject.

6. The kit of claim 1, wherein the sample obtained from the human subject comprises peripheral blood CD4+ T-cells.

7. The kit of claim 1, wherein the human subject has a skin lesion.

8. The kit of claim 7, wherein the sample obtained from the human subject comprises cells of the skin lesion.

* * * * *